(12) United States Patent
Yanagihara

(10) Patent No.: US 9,423,869 B2
(45) Date of Patent: Aug. 23, 2016

(54) OPERATION SUPPORT DEVICE

(71) Applicant: OLYMPUS CORPORATION, Tokyo (JP)

(72) Inventor: Masaru Yanagihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/157,920

(22) Filed: Jan. 17, 2014

(65) Prior Publication Data

US 2014/0135795 A1  May 15, 2014

Related U.S. Application Data

(63) Continuation of application No. PCT/JP2012/070414, filed on Aug. 3, 2012.

(60) Provisional application No. 61/515,203, filed on Aug. 4, 2011.

(30) Foreign Application Priority Data

Jan. 24, 2012 (JP) ................................ 2012-012104

(51) Int. Cl.
*G06F 3/00* (2006.01)
*G06F 3/01* (2006.01)
(Continued)

(52) U.S. Cl.
CPC . *G06F 3/01* (2013.01); *A61B 17/29* (2013.01); *A61B 17/32002* (2013.01);
(Continued)

(58) Field of Classification Search
CPC ........ B25J 5/007; B25J 9/0003; B25J 9/1697; B25J 13/083; B25J 9/1612; B25J 9/1633; B25J 13/08; B25J 13/084; B25J 13/082; B25J 13/085; B25J 15/0009; B25J 15/00; B25J 3/00; B25J 9/00; B25J 15/0206; B25J 19/021; B25J 9/126; B25J 15/0253; B25J 15/0246; B65G 2203/041; G05B 2219/39387; G05B 2219/39505; G05B 2219/39523; G05B 2219/40138; G05B 2219/40619; G05B 2219/45117; G05B 2219/39528; G05B 2219/40053; G05B 2219/40571; A61B 19/2203; A61B 2019/2223; A61B 2019/2292; A61B 2019/2296; G06F 3/016; B23Q 15/225; G01L 5/226; Y10S 294/907; Y10S 901/09
See application file for complete search history.

(56) References Cited

U.S. PATENT DOCUMENTS 3,139,990 A    7/1964  Jelatis et al.
3,923,166 A *  12/1975 Fletcher ................. B25J 19/002
                                                  414/4
(Continued)

FOREIGN PATENT DOCUMENTS

CN    101027010 A    8/2007
CN    101167658 A    4/2008
(Continued)

OTHER PUBLICATIONS

English Abstract of JP 01-234140 dated Sep. 19, 1989.
(Continued)

*Primary Examiner* — Jonathan L Sample
(74) *Attorney, Agent, or Firm* — Scully, Scott, Murphy & Presser, P.C.

(57) ABSTRACT

An operation support device includes an operation part in which the operation input is performed by an operator, an action part to which a surgical tool is attached and which is driven by the operation input, a drive source that is provided in the operation part, and generates a driving force which adjusts the manipulation resistance at the time of the operation input, and a control unit that sets the magnitude and direction of the driving force, wherein the control unit sets the magnitude and direction of the driving force based on the operation input to the operation part.

10 Claims, 6 Drawing Sheets

(51) Int. Cl.
*A61B 17/29* (2006.01)
*A61B 17/32* (2006.01)
*A61B 18/14* (2006.01)
*B25J 13/02* (2006.01)
*A61B 17/068* (2006.01)
*A61B 17/00* (2006.01)

(52) U.S. Cl.
CPC ............ *A61B 18/1402* (2013.01); *B25J 13/02* (2013.01); *A61B 17/068* (2013.01); *A61B 46/23* (2016.02); *A61B 2017/00119* (2013.01); *A61B 2017/00477* (2013.01); *A61B 2017/00482* (2013.01); *Y10S 901/08* (2013.01); *Y10S 901/09* (2013.01); *Y10S 901/30* (2013.01); *Y10T 29/49826* (2015.01); *Y10T 74/18056* (2015.01)

(56) References Cited

U.S. PATENT DOCUMENTS

| | | | | |
|---|---|---|---|---|
| 4,672,281 | A * | 6/1987 | Yagusic | B23Q 15/225 318/562 |
| 4,830,569 | A | 5/1989 | Jannborg | |
| 4,872,803 | A * | 10/1989 | Asakawa | B25J 9/1015 294/119.1 |
| 5,214,969 | A * | 6/1993 | Adkins | A24C 5/32 131/908 |
| 5,603,723 | A | 2/1997 | Aranyi et al. | |
| 5,632,432 | A | 5/1997 | Schulze et al. | |
| 5,649,956 | A * | 7/1997 | Jensen | B25J 9/1065 403/316 |
| 5,656,903 | A | 8/1997 | Shui et al. | |
| 5,712,543 | A | 1/1998 | Sjostrom | |
| 5,760,530 | A * | 6/1998 | Kolesar | H01L 41/1132 310/317 |
| 5,762,458 | A | 6/1998 | Wang et al. | |
| 5,784,542 | A * | 7/1998 | Ohm | B25J 3/04 700/247 |
| 5,817,119 | A | 10/1998 | Klieman et al. | |
| 5,836,869 | A | 11/1998 | Kudo et al. | |
| 5,855,583 | A | 1/1999 | Wang et al. | |
| 5,871,493 | A | 2/1999 | Sjostrom et al. | |
| 5,876,325 | A | 3/1999 | Mizuno et al. | |
| 6,007,550 | A | 12/1999 | Wang et al. | |
| 6,063,095 | A | 5/2000 | Wang et al. | |
| 6,082,797 | A * | 7/2000 | Antonette | B25J 9/104 294/103.1 |
| 6,090,122 | A | 7/2000 | Sjostrom et al. | |
| 6,102,850 | A | 8/2000 | Wang et al. | |
| 6,132,368 | A | 10/2000 | Cooper | |
| 6,132,441 | A | 10/2000 | Grace | |
| 6,206,903 | B1 | 3/2001 | Ramans | |
| 6,246,200 | B1 | 6/2001 | Blumenkranz et al. | |
| 6,328,752 | B1 | 12/2001 | Sjostrom et al. | |
| 6,346,072 | B1 | 2/2002 | Cooper | |
| 6,430,473 | B1 | 8/2002 | Lee et al. | |
| 6,436,107 | B1 | 8/2002 | Wang et al. | |
| 6,441,577 | B2 | 8/2002 | Blumenkranz et al. | |
| 6,557,558 | B1 | 5/2003 | Tajima et al. | |
| 6,574,355 | B2 * | 6/2003 | Green | H04N 13/0497 348/E13.014 |
| 6,587,750 | B2 | 7/2003 | Gerbi et al. | |
| 6,602,185 | B1 | 8/2003 | Uchikubo | |
| 6,645,196 | B1 | 11/2003 | Nixon et al. | |
| 6,666,876 | B2 | 12/2003 | Kawai et al. | |
| 6,676,684 | B1 | 1/2004 | Morley et al. | |
| 6,685,698 | B2 | 2/2004 | Morley et al. | |
| 6,699,177 | B1 | 3/2004 | Laby et al. | |
| 6,746,443 | B1 | 6/2004 | Morley et al. | |
| 6,783,524 | B2 | 8/2004 | Anderson et al. | |
| 6,786,896 | B1 | 9/2004 | Madhani et al. | |
| 6,853,879 | B2 | 2/2005 | Sunaoshi | |
| 6,866,671 | B2 | 3/2005 | Tierney et al. | |
| 6,905,460 | B2 | 6/2005 | Wang et al. | |
| 6,913,613 | B2 | 7/2005 | Schwarz et al. | |
| 7,083,571 | B2 | 8/2006 | Wang et al. | |
| 7,101,363 | B2 | 9/2006 | Nishizawa et al. | |
| 7,107,124 | B2 | 9/2006 | Green | |
| 7,118,582 | B1 | 10/2006 | Wang et al. | |
| 7,273,488 | B2 | 9/2007 | Nakamura et al. | |
| 7,295,893 | B2 | 11/2007 | Sunaoshi | |
| 7,313,464 | B1 * | 12/2007 | Perreault | B25J 9/1666 318/568.1 |
| 7,331,967 | B2 | 2/2008 | Lee et al. | |
| 7,357,774 | B2 | 4/2008 | Cooper | |
| 7,373,219 | B2 | 5/2008 | Nowlin et al. | |
| 7,422,592 | B2 | 9/2008 | Morley et al. | |
| 7,476,237 | B2 | 1/2009 | Taniguchi et al. | |
| 7,549,998 | B2 | 6/2009 | Braun | |
| 7,594,912 | B2 | 9/2009 | Cooper et al. | |
| 7,608,083 | B2 | 10/2009 | Lee et al. | |
| 7,654,431 | B2 | 2/2010 | Hueil et al. | |
| 7,666,191 | B2 | 2/2010 | Orban, III et al. | |
| 7,674,255 | B2 | 3/2010 | Braun | |
| 7,695,481 | B2 | 4/2010 | Wang et al. | |
| 7,699,835 | B2 | 4/2010 | Lee et al. | |
| 7,699,855 | B2 | 4/2010 | Anderson et al. | |
| 7,778,733 | B2 | 8/2010 | Nowlin et al. | |
| 7,819,884 | B2 | 10/2010 | Lee et al. | |
| 7,819,885 | B2 | 10/2010 | Cooper | |
| 7,862,579 | B2 | 1/2011 | Ortiz et al. | |
| 7,865,266 | B2 | 1/2011 | Moll et al. | |
| 7,955,321 | B2 | 6/2011 | Kishi et al. | |
| 8,105,320 | B2 | 1/2012 | Manzo | |
| 8,155,479 | B2 | 4/2012 | Hoffman et al. | |
| 8,267,958 | B2 | 9/2012 | Braun | |
| 8,350,806 | B2 * | 1/2013 | Nagasaka | G06F 3/016 345/156 |
| 8,423,186 | B2 | 4/2013 | Itkowitz et al. | |
| 8,460,277 | B2 | 6/2013 | Suarez et al. | |
| 8,496,647 | B2 | 7/2013 | Blumenkranz et al. | |
| 8,540,748 | B2 | 9/2013 | Murphy et al. | |
| 8,744,137 | B2 | 6/2014 | Sakai et al. | |
| 8,845,681 | B2 | 9/2014 | Grace | |
| 8,876,858 | B2 | 11/2014 | Braun | |
| 8,888,789 | B2 * | 11/2014 | Prisco | A61B 17/0218 606/130 |
| 8,903,549 | B2 | 12/2014 | Itkowitz et al. | |
| 8,906,002 | B2 | 12/2014 | Kishi et al. | |
| 9,039,681 | B2 | 5/2015 | Wang et al. | |
| 9,283,675 | B2 | 3/2016 | Hager et al. | |
| 9,308,009 | B2 | 4/2016 | Madan et al. | |
| 9,308,646 | B2 * | 4/2016 | Lim | B25J 9/1633 |
| 2001/0021859 | A1 | 9/2001 | Kawai et al. | |
| 2001/0055062 | A1 | 12/2001 | Shioda et al. | |
| 2002/0072736 | A1 | 6/2002 | Tierney et al. | |
| 2002/0091374 | A1 | 7/2002 | Cooper | |
| 2002/0128552 | A1 | 9/2002 | Nowlin et al. | |
| 2003/0033024 | A1 | 2/2003 | Sunaoshi | |
| 2003/0060927 | A1 | 3/2003 | Gerbi et al. | |
| 2003/0069471 | A1 | 4/2003 | Nakanishi et al. | |
| 2003/0083648 | A1 | 5/2003 | Wang et al. | |
| 2003/0100817 | A1 | 5/2003 | Wang et al. | |
| 2003/0216723 | A1 | 11/2003 | Shinmura et al. | |
| 2004/0092912 | A1 | 5/2004 | Jinno et al. | |
| 2004/0111113 | A1 | 6/2004 | Nakamura et al. | |
| 2004/0140787 | A1 * | 7/2004 | Okamoto | B25J 13/083 318/568.21 |
| 2004/0186345 | A1 | 9/2004 | Wang et al. | |
| 2004/0186624 | A1 * | 9/2004 | Oda | B25J 9/1697 700/245 |
| 2004/0243147 | A1 * | 12/2004 | Lipow | A61B 90/36 606/130 |
| 2004/0246469 | A1 | 12/2004 | Hirose | |
| 2005/0020876 | A1 | 1/2005 | Shioda et al. | |
| 2005/0021050 | A1 | 1/2005 | Cooper | |
| 2005/0033117 | A1 | 2/2005 | Ozaki et al. | |
| 2005/0125027 | A1 | 6/2005 | Knodel et al. | |
| 2005/0149003 | A1 | 7/2005 | Tierney et al. | |
| 2005/0228365 | A1 | 10/2005 | Wang et al. | |
| 2005/0273086 | A1 * | 12/2005 | Green | A61B 19/2203 606/1 |
| 2006/0052664 | A1 | 3/2006 | Julian et al. | |
| 2006/0074408 | A1 | 4/2006 | Jinno et al. | |

(56) References Cited

U.S. PATENT DOCUMENTS

| | | |
|---|---|---|
| 2006/0079865 A1 | 4/2006 | Jinno et al. |
| 2006/0079866 A1 | 4/2006 | Jinno et al. |
| 2006/0087746 A1 | 4/2006 | Lipow |
| 2006/0116973 A1* | 6/2006 | Okamoto ............... B25J 5/007 706/16 |
| 2006/0149162 A1 | 7/2006 | Daw et al. |
| 2006/0155262 A1 | 7/2006 | Kishi et al. |
| 2006/0161138 A1 | 7/2006 | Orban, III et al. |
| 2006/0190031 A1 | 8/2006 | Wales et al. |
| 2006/0235436 A1 | 10/2006 | Anderson et al. |
| 2007/0012135 A1 | 1/2007 | Tierney et al. |
| 2007/0089557 A1 | 4/2007 | Solomon et al. |
| 2007/0119274 A1 | 5/2007 | Devengenzo et al. |
| 2007/0137372 A1 | 6/2007 | Devengenzo et al. |
| 2007/0138992 A1* | 6/2007 | Prisco .................... A61B 19/22 318/568.21 |
| 2007/0142823 A1* | 6/2007 | Prisco .................... A61B 19/22 606/1 |
| 2007/0142825 A1* | 6/2007 | Prisco .................... A61B 19/22 606/1 |
| 2007/0156122 A1* | 7/2007 | Cooper ............... A61B 19/2203 606/1 |
| 2007/0167679 A1 | 7/2007 | Miyamoto et al. |
| 2007/0167680 A1 | 7/2007 | Miyamoto et al. |
| 2007/0173689 A1 | 7/2007 | Ozaki et al. |
| 2007/0197896 A1 | 8/2007 | Moll et al. |
| 2007/0208375 A1 | 9/2007 | Nishizawa et al. |
| 2007/0219668 A1* | 9/2007 | Takahashi ............ B25J 15/0009 700/249 |
| 2007/0225550 A1 | 9/2007 | Gattani et al. |
| 2007/0249897 A1 | 10/2007 | Miyamoto et al. |
| 2007/0265638 A1* | 11/2007 | Lipow .................... A61B 90/36 606/130 |
| 2008/0015611 A1 | 1/2008 | Jinno et al. |
| 2008/0033240 A1 | 2/2008 | Hoffman et al. |
| 2008/0046122 A1 | 2/2008 | Manzo et al. |
| 2008/0051631 A1 | 2/2008 | Dejima et al. |
| 2008/0059131 A1* | 3/2008 | Tokita .................... G06F 3/011 703/5 |
| 2008/0103524 A1 | 5/2008 | Grace |
| 2008/0140088 A1 | 6/2008 | Orban, III |
| 2008/0147091 A1 | 6/2008 | Cooper |
| 2008/0177285 A1 | 7/2008 | Brock et al. |
| 2008/0204425 A1* | 8/2008 | Nagasaka ............... G06F 3/016 345/173 |
| 2008/0215065 A1 | 9/2008 | Wang et al. |
| 2008/0228196 A1 | 9/2008 | Wang et al. |
| 2008/0234866 A1 | 9/2008 | Kishi et al. |
| 2008/0243142 A1 | 10/2008 | Gildenberg |
| 2008/0262654 A1 | 10/2008 | Omori et al. |
| 2008/0287735 A1 | 11/2008 | Takemoto et al. |
| 2008/0312668 A1 | 12/2008 | Grace |
| 2009/0018700 A1* | 1/2009 | Okamoto ............... B25J 13/083 700/260 |
| 2009/0022262 A1 | 1/2009 | Ohishi |
| 2009/0030273 A1 | 1/2009 | Murakami |
| 2009/0034820 A1 | 2/2009 | Sugiyama |
| 2009/0036736 A1 | 2/2009 | Dejima et al. |
| 2009/0036902 A1 | 2/2009 | DiMaio et al. |
| 2009/0046146 A1 | 2/2009 | Hoyt |
| 2009/0057369 A1 | 3/2009 | Smith et al. |
| 2009/0088634 A1 | 4/2009 | Zhao et al. |
| 2009/0088773 A1 | 4/2009 | Zhao et al. |
| 2009/0088897 A1 | 4/2009 | Zhao et al. |
| 2009/0132088 A1* | 5/2009 | Taitler .................... G05B 19/42 700/264 |
| 2009/0163948 A1 | 6/2009 | Sunaoshi et al. |
| 2009/0171147 A1 | 7/2009 | Lee et al. |
| 2009/0182193 A1 | 7/2009 | Whitman et al. |
| 2009/0193299 A1 | 7/2009 | Sekiguchi et al. |
| 2009/0204911 A1 | 8/2009 | Sekiguchi et al. |
| 2009/0247877 A1 | 10/2009 | Tanaka et al. |
| 2009/0281378 A1* | 11/2009 | Banju ................... A61B 1/00133 600/106 |
| 2009/0326318 A1 | 12/2009 | Tognaccini et al. |
| 2010/0010673 A1 | 1/2010 | Wang et al. |
| 2010/0013812 A1 | 1/2010 | Gu et al. |
| 2010/0087835 A1 | 4/2010 | Blumenkranz et al. |
| 2010/0160728 A1* | 6/2010 | Yoshie ............... A61B 1/00147 600/109 |
| 2010/0163057 A1 | 7/2010 | Anderson et al. |
| 2010/0174293 A1 | 7/2010 | Orban, III et al. |
| 2010/0217284 A1 | 8/2010 | Grace |
| 2010/0217528 A1* | 8/2010 | Sato ...................... B25J 9/1666 701/301 |
| 2010/0225209 A1 | 9/2010 | Goldberg et al. |
| 2010/0228264 A1 | 9/2010 | Robinson et al. |
| 2010/0228265 A1 | 9/2010 | Prisco |
| 2010/0234857 A1 | 9/2010 | Itkowitz et al. |
| 2010/0274087 A1 | 10/2010 | Diolaiti et al. |
| 2010/0291520 A1* | 11/2010 | Kurenov ............ A61B 17/0469 434/262 |
| 2010/0317965 A1 | 12/2010 | Itkowitz et al. |
| 2010/0318099 A1 | 12/2010 | Itkowitz et al. |
| 2010/0318101 A1 | 12/2010 | Choi |
| 2010/0332031 A1 | 12/2010 | Itkowitz et al. |
| 2011/0015650 A1 | 1/2011 | Choi et al. |
| 2011/0050852 A1 | 3/2011 | Lamprecht et al. |
| 2011/0118707 A1 | 5/2011 | Burbank |
| 2011/0118748 A1 | 5/2011 | Itkowitz |
| 2011/0118753 A1 | 5/2011 | Itkowitz et al. |
| 2011/0137337 A1 | 6/2011 | van den Dool et al. |
| 2011/0190932 A1* | 8/2011 | Tsusaka .................. B25J 13/08 700/254 |
| 2011/0230894 A1 | 9/2011 | Simaan et al. |
| 2011/0238079 A1 | 9/2011 | Hannaford et al. |
| 2011/0276058 A1 | 11/2011 | Choi et al. |
| 2011/0279374 A1* | 11/2011 | Park ....................... G06F 3/016 345/168 |
| 2011/0282493 A1 | 11/2011 | Ortmaier |
| 2011/0288579 A1 | 11/2011 | Hyodo |
| 2011/0306952 A1 | 12/2011 | Chen et al. |
| 2012/0071752 A1* | 3/2012 | Sewell .................... A61B 6/12 600/424 |
| 2012/0165828 A1 | 6/2012 | Duque et al. |
| 2012/0191245 A1* | 7/2012 | Fudaba ................. B25J 9/1633 700/254 |

FOREIGN PATENT DOCUMENTS

| | | |
|---|---|---|
| CN | 101426412 A | 5/2009 |
| DE | 10 2008 041 867 A1 | 3/2010 |
| EP | 0 677 278 A1 | 10/1995 |
| EP | 1 728 475 A2 | 12/2006 |
| EP | 2 092 875 A1 | 8/2009 |
| EP | 2 298 220 A1 | 3/2011 |
| EP | 2 332 484 A2 | 6/2011 |
| JP | 63-029810 A | 2/1988 |
| JP | 64-034688 A | 2/1989 |
| JP | 01-271185 A | 10/1989 |
| JP | 02-071980 A | 3/1990 |
| JP | 02-292193 A | 12/1990 |
| JP | 03-161289 A | 7/1991 |
| JP | 05-096477 A | 4/1993 |
| JP | 5-329784 A | 12/1993 |
| JP | 07-001366 A | 1/1995 |
| JP | 07-194609 A | 8/1995 |
| JP | 07-241300 A | 9/1995 |
| JP | 07-246578 A | 9/1995 |
| JP | 07-096182 B2 | 10/1995 |
| JP | 8-66883 A | 3/1996 |
| JP | 08-215204 A | 8/1996 |
| JP | 08-243080 A | 9/1996 |
| JP | 10-128538 A | 5/1998 |
| JP | 11-300662 A | 11/1999 |
| JP | 2000-312684 A | 11/2000 |
| JP | 2001-087281 A | 4/2001 |
| JP | 2001-113481 A | 4/2001 |
| JP | 2001-277157 A | 10/2001 |
| JP | 2001-309920 A | 11/2001 |
| JP | 2002-014287 A | 1/2002 |
| JP | 2002-059380 A | 2/2002 |
| JP | 2002-102248 A | 4/2002 |
| JP | 2002-272758 A | 9/2002 |

(56) References Cited

FOREIGN PATENT DOCUMENTS

| | | |
|---|---|---|
| JP | 2002-537884 A | 11/2002 |
| JP | 2003-024336 A | 1/2003 |
| JP | 2003-053685 A | 2/2003 |
| JP | 2003-250812 A | 9/2003 |
| JP | 2003-265500 A | 9/2003 |
| JP | 2003-340752 A | 12/2003 |
| JP | 2004-105451 A | 4/2004 |
| JP | 2004-114201 A | 4/2004 |
| JP | 2005-511185 A | 4/2005 |
| JP | 2005-192743 A | 7/2005 |
| JP | 3686947 B2 | 8/2005 |
| JP | 2005-261827 A | 9/2005 |
| JP | 2005-312991 A | 11/2005 |
| JP | 2006-061272 A | 3/2006 |
| JP | 2006-167867 A | 6/2006 |
| JP | 2006-288955 A | 10/2006 |
| JP | 2006-321027 A | 11/2006 |
| JP | 2007-029274 A | 2/2007 |
| JP | 2007-038315 A | 2/2007 |
| JP | 2007-98507 A | 4/2007 |
| JP | 2007-105485 A | 4/2007 |
| JP | 3999816 B2 | 10/2007 |
| JP | 2008-000282 A | 1/2008 |
| JP | 2008-036793 A | 2/2008 |
| JP | 4058113 B2 | 3/2008 |
| JP | 2008-093270 A | 4/2008 |
| JP | 2008-173724 A | 7/2008 |
| JP | 4129313 B | 8/2008 |
| JP | 4176126 B2 | 11/2008 |
| JP | 2009-028157 A | 2/2009 |
| JP | 2009-056164 A | 3/2009 |
| JP | 2009-512514 A | 3/2009 |
| JP | 2009-520573 A | 5/2009 |
| JP | 2009-178230 A | 8/2009 |
| JP | 2009-178541 A | 8/2009 |
| JP | 2009-530037 A | 8/2009 |
| JP | 2009-195694 A | 9/2009 |
| JP | 2009-226093 A | 10/2009 |
| JP | 2009-269127 A | 11/2009 |
| JP | 2010-504127 A | 2/2010 |
| JP | 2010-076012 A | 4/2010 |
| JP | 2010-524548 A | 7/2010 |
| JP | 2011-509112 A | 3/2011 |
| JP | 2011-206213 A | 10/2011 |
| JP | 2012-000199 A | 1/2012 |
| JP | 2012-012104 A | 1/2012 |
| JP | 2012-091310 A | 5/2012 |
| JP | WO 2013018930 A1 * | 2/2013 ......... A61B 19/2203 |
| WO | 97/16123 A1 | 5/1997 |
| WO | 97/16124 A1 | 5/1997 |
| WO | 97/29690 A1 | 8/1997 |
| WO | 98/25666 A1 | 6/1998 |
| WO | WO 00/51486 A1 | 9/2000 |
| WO | 00/60421 A2 | 10/2000 |
| WO | WO 03/049596 A2 | 6/2003 |
| WO | 2006/111966 A2 | 10/2006 |
| WO | WO 2007/047782 A2 | 4/2007 |
| WO | WO 2007/075864 A1 | 7/2007 |
| WO | WO 2007/111955 A2 | 10/2007 |
| WO | WO 2007/126443 A2 | 11/2007 |
| WO | WO 2007/138674 A1 | 12/2007 |
| WO | WO 2008/038184 A2 | 4/2008 |
| WO | WO 2008/108289 A1 | 9/2008 |
| WO | WO 2009034477 A2 | 3/2009 |
| WO | 2009/089614 A1 | 7/2009 |
| WO | WO 2010006057 A1 | 1/2010 |
| WO | 2010/093152 A2 | 8/2010 |
| WO | WO 2010109932 A1 | 9/2010 |
| WO | 2011/025786 A1 | 3/2011 |
| WO | 2011/060139 A2 | 5/2011 |
| WO | 2011/060185 A1 | 5/2011 |
| WO | 2011/060187 A1 | 5/2011 |
| WO | 2011/085815 A1 | 7/2011 |
| WO | WO 2012/042949 A1 | 4/2012 |

OTHER PUBLICATIONS

English Abstract of WO 0051486 A1 dated Sep. 8, 2000.
International Search Report dated Oct. 23, 2012 issued in PCT/JP2012/070414.
International Search Report dated Sep. 4, 2012 issued in PCT/JP2012/070408.
International Search Report dated Aug. 28, 2012 issued in PCT/JP2012/069927.
International Search Report dated Sep. 4, 2012 issued in PCT/JP2012/070415.
International Search Report dated Oct. 16, 2012 issued in PCT/JP2012/070581.
International Search Report dated Nov. 13, 2012 issued in PCT/JP2012/070576.
International Search Report dated Sep. 18, 2012 issued in PCT/JP2012/070417.
International Search Report dated Oct. 30, 2012 issued in PCT/JP2012/070418.
International Search Report dated Sep. 11, 2012 issued in PCT/JP2012/070416.
International Search Report dated Sep. 18, 2012 issued in PCT/JP2012/070407.
International Search Report dated Sep. 18, 2012 issued in PCT/JP2012/069868.
International Search Report dated Nov. 6, 2012 issued in PCT/JP2012/069919.
International Search Report dated Sep. 11, 2012 issued in PCT/JP2012/069696.
Chinese Office Action dated Jun. 3, 2015 from related Chinese Application No. 201280035926.3, together with an English language translation.
Chinese Office Action dated Jul. 1, 2015 from related Chinese Application No. 201280037244.6, together with an English language translation.
Extended Supplementary European Search Report dated Jul. 1, 2015 from related European Application No. 12 82 0066.4.
Extended Supplementary European Search Report dated Jul. 2, 2015 from related European Application No. 12 81 9672.2.
Extended Supplementary European Search Report dated Jul. 23, 2015 from related European Application No. 12 81 9455.2.
Office Action dated Oct. 19, 2015 received in related U.S. Patent Application, namely U.S. Appl. No. 14/168,525.
Office Action dated Oct. 22, 2015 received in related U.S. Patent Application, namely U.S. Appl. No. 14/151,987.
U.S. Office Action dated Apr. 9, 2015 received in related U.S. Patent Application, namely U.S. Appl. No. 14/169,675.
Office Action dated Sep. 16, 2015 received in related U.S. Patent Application, namely U.S. Appl. No. 13/566,012.
Notice of Allowance dated Jan. 20, 2015 from related U.S. Appl. No. 13/566,023.
Notice of Allowance dated Jan. 29, 2015 from related U.S. Appl. No. 14/168,551.
Extended Supplementary European Search Report dated Feb. 12, 2015 from related European Application No. 12 81 9447.9.
Extended Supplementary European Search Report dated Feb. 13, 2015 from related European Application No. 12 82 0679.4.
Supplementary European Search Report dated Feb. 18, 2015 from related European Application No. 12 82 0758.6.
Extended Supplementary European Search Report dated Feb. 23, 2015 from related European Application No. 12 81 9877.7.
Extended Supplementary European Search Report dated Feb. 23, 2015 from related European Application No. 12 82 0239.7.
Partial Supplementary European Search Report dated Feb. 26, 2015 from related European Application No. 12 82 0066.4.
Partial Supplementary European Search Report dated Feb. 27, 2015 from related European Application No. 12 81 9672.2.
Extended Supplementary European Search Report dated Mar. 2, 2015 from related European Application No. 12 82 0017.7.
Extended Supplementary European Search Report dated Mar. 16, 2015 from related European Application No. 12 82 0479.9.
Extended Supplementary European Search Report dated Mar. 16, 2015 from related European Application No. 12 81 9504.7.

(56) References Cited

OTHER PUBLICATIONS

Extended Supplementary European Search Report dated Mar. 16, 2015 from related European Application No. 12 81 9398.4.
Office Action dated Mar. 25, 2015 received in related U.S. Patent Application, namely U.S. Appl. No. 14/169,321.
Extended Supplementary European Search Report dated Mar. 27, 2015 from related European Application No. 12 82 0056.5.
Office Action dated Feb. 22, 2016 received in related U.S. Appl. No. 14/166,496.
Office Action dated Mar. 10, 2016 received in related U.S. Appl. No. 13/566,012.
Japanese Office Action dated Jan. 19, 2016 from related Japanese Patent Application No. 2012-036226, together with an English language translation.
Office Action dated Mar. 24, 2016 received in related U.S. Appl. No. 13/566,047.
Office Action dated May 9, 2016 received in related U.S. Appl. No. 14/170,856.
Japanese Office Action dated Jun. 14, 2016 in related Japanese Patent Application No. 2012-012104.
Office Action dated Jun. 16, 2016 received in related U.S. Appl. No. 14/169,742.
European Patent Office Communication dated May 23, 2016 in related European Application No. 12 819 877.7.

\* cited by examiner

OPERATION SUPPORT DEVICE

This application is a continuation application based on PCT Patent Application No. PCT/JP2012/070414, filed Aug. 3, 2012, claiming priority based on Provisional Application No. 61/515,203 filed in US on Aug. 4, 2011, and Japanese Patent Application No. 2012-012104 filed on Jan. 24, 2012, the contents of which are incorporated herein by reference.

BACKGROUND OF THE INVENTION

1. Field of the Invention

The present invention relates to an operation support device, and more specifically, to an operation support device in which a manipulation resistance during an operation input is adjusted by a driving force.

2. Description of the Related Art

In the past, a master slave manipulator which operates a slave manipulator by a remote operation using a master manipulator has been known, and application to an operation support device or the like has been suggested. Japanese Unexamined Patent Application, First Publication No. 2006-167867 discloses a remote operation device capable of being used in such an application.

In the remote operation device of Japanese Unexamined Patent Application, First Publication No. 2006-167867, a distance between a slave hand and a work object is detected, and an automatic mode in which the slave hand is automatically moved and a manual mode in which the slave hand is moved based on the operation of a master hand is switched using a value of the detected distance. When the distance between the work object and the slave hand is far, the slave hand approaches the work object in the automatic mode. When the distance between the slave hand and the work object is equal to or less than a predetermined value, the mode is switched to the manual mode, and a user can operate the slave hand. As a consequence, when the slave hand is considerably far from the work object, the user need not operate the master hand, and the burden on the user is reduced.

Furthermore, Japanese Unexamined Patent Application, First Publication No. 2006-167867 also discloses that reaction feedback to the master hand is changed depending on the distance between the slave hand and the work object, and a manipulation resistance is changed when the user operates the master hand. Thus, when the slave hand approaches the work object, the user can easily perform a delicate operation.

There are various operations for a target tissue in the operation. For example, there are an operation that requires a minute and accurate operation, like a motion of applying a needle when sewing the tissue, and for example, a treatment to stop bleeding of a bleeding that occurred during the operation, an operation that requires the rapid performance of a series of motions from the identification of a bleeding part to the completion of hemostasis.

In the former case, it is known that, by applying suitable resistance (hereinafter referred to as a "manipulation resistance") to the operation of the master manipulator, jiggling hand of a user and feeling of instability of the hand are reduced, and thus the operation can be easily performed. The magnitude of the optimal manipulation resistance is mainly defined by the contents of the operation.

SUMMARY OF THE INVENTION

According to a first aspect of the invention, an operation support device includes an operation part that performs an operation input by an operator, and an action part to which a surgical tool is attached and which is driven by the operation input. Moreover, the operation support device further includes a drive source that is provided in the operation part and generates a driving force which adjusts the manipulation resistance at the time of the operation input, and a control unit that sets a magnitude and a direction of the driving force, wherein the control unit sets the magnitude and the direction of the driving force based on the operation input to the operation part. In addition, the term "force" of the term "the driving force" includes torque.

According to a second aspect of the invention, in the operation support device according to the first aspect, the operation part may have a switch, the control unit sets the driving force based on one of a plurality of modes, and when the switch is operated by the operator, the mode used when the control unit sets the driving force is switched.

According to a third aspect of the invention, in the operation support device according to the second aspect, the switch may be configured to be operated by a hand or a foot of the operator.

According to a fourth aspect of the invention, in the operation support device according to the second or third aspect, the surgical tool may be in an active state when performing the operation, and the switch may combine function to switch the surgical tool to the active state.

According to a fifth aspect of the invention, in the operation support device according to any one of the first to fourth aspects, the operation support device may further include a detection part that detects an amount of motion of the operation part using the operation input, and the control unit may set the driving force so that the driving force is increased as the amount of motion is reduced.

According to a sixth aspect of the invention, in the operation support device according to the fifth aspect, the control unit may set the driving force so as to relatively increase when the amount of motion is equal to or less than a predetermined threshold value.

According to a seventh aspect of the invention, in the operation support device according to any one of the first to fourth aspects, the device may further include a detection part that detects the amount of motion of the operation part using the operation input, and the control unit may set the driving force so that the driving force is increased as the amount of motion is increased and a relationship between an amount of change of the amount of motion and an amount of change of the driving force is changed depending on a value of the amount of motion.

According to an eighth aspect of the invention, in the operation support device according to the seventh aspect, the control unit may set the driving force so as to relatively increase when the amount of motion is equal to or greater than a predetermined threshold value.

According to a ninth aspect of the invention, in the operation support device according to any one of the first to eighth aspects, the surgical tool may be attachably and detachably provided in a plural number in the action part, the respective surgical tool may have identification information, and the control unit may set magnitude and direction of the driving force based on the identification information of the surgical tool mounted on the action part.

DETAILED DESCRIPTION OF THE INVENTION

Figure 1:
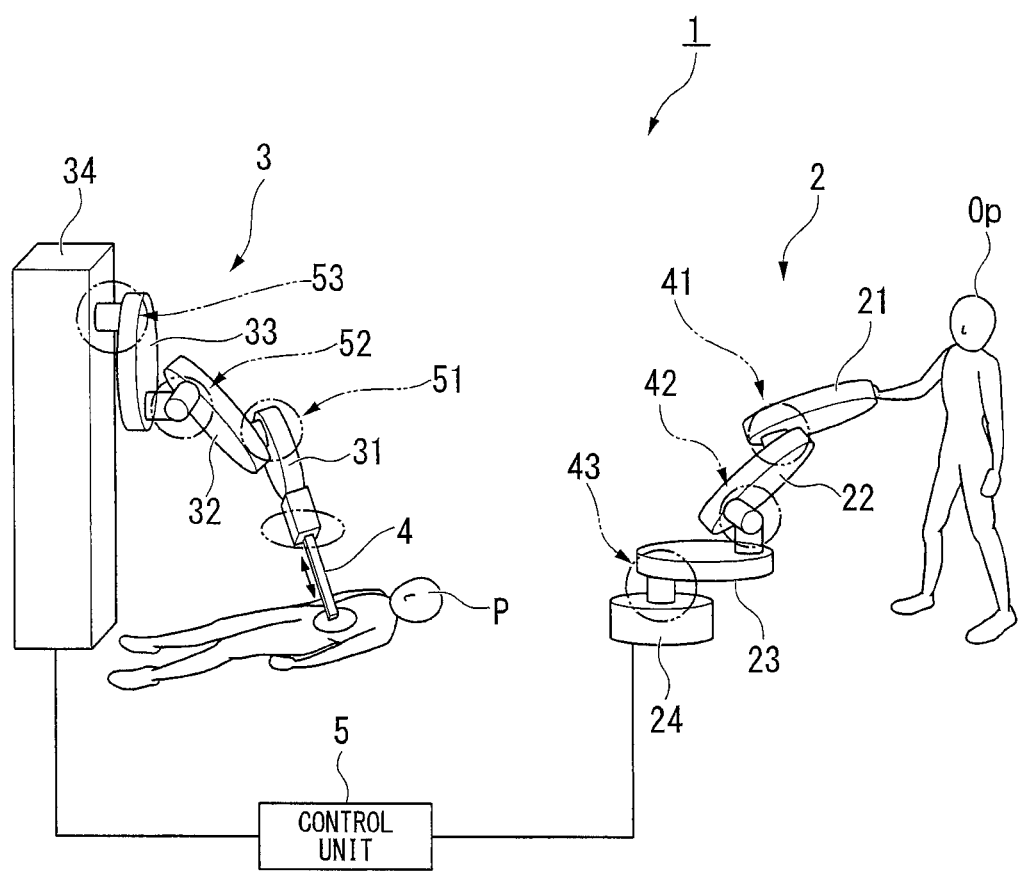
FIG. 1 is a diagram showing a master slave manipulator to which a motion mechanism according to a first embodiment of the invention is applied.

Hereinafter, a first embodiment of the invention will be described. FIG. 1 is a diagram that shows a schematic configuration of a medical master slave manipulator 1 that is an operation support device according to the first embodiment.

The master slave manipulator 1 includes a master arm (an operation part) 2 operated by an operator Op, and a slave arm (an action part) 3 that is operated in synchronization with the master arm 2. A surgical tool 4 is attached to a distal end of the slave arm 3, and various operations are performed on a patient P using the surgical tool 4.

The master arm 2 has three arms including a first master arm 21, a second master arm 22, and a third master arm 23. The first master arm 21 and the second master arm 22 are connected to each other by a first joint part 41 in a relatively rotatable manner. The second master arm 22 and the third master arm 23 are connected to each other by a second joint part 42 in a relatively rotatable manner. Furthermore, the third master arm 23 is connected to a base 24 supporting the master arm 2 by a base joint part 43 in a relatively rotatable manner. The master arm 2 is configured to be able to perform a multiaxial rotational movement as a whole.

The slave arm 3 has three arms including a first slave arm 31, a second slave arm 32 and a third slave arm 33. The first slave arm 31 and the second slave arm 32 are connected to each other by a third joint part 51 in a relatively rotatable manner. The second slave arm 32 and the third slave arm 33 are connected to each other by a fourth joint part 52 in a relatively rotatable manner. The third slave arm 33 is connected to a housing section 34 including a driving force transmission member or the like by a second base joint part 53 in a relatively rotatable manner. The respective joint parts 51, 52, and 53 are configured to be capable of performing the rotational drive by a drive source (not shown).

The master arm 2 and the slave arm 3 are connected to each other via a control unit 5. The control unit 5 generates a manipulation signal for manipulating the slave arm 3 based on an operation input to the master arm 2 by the operator Op, and sends the manipulation signal to the slave arm 3. As an example of a method of processing the operation input for generating the manipulation signal, there is a method of changing a scale of the movement of the master arm and the slave arm based on the manipulation signal which is set an angle in which a scale is changed corresponding to a gear ratio by gears provided in each joint part of the master arm. Furthermore, the control unit 5 adjusts the manipulation resistance in which the operator Op receives when the operator Op performs the operation input to the master arm 2 based on the operation input to the master arm 2. The details of the adjustment will be described later.

When the operator Op operates the master arm 2 and performs various operations using the slave arm 3, the respective joint parts 51, 52, and 53 of the slave arm 3 are operated by the driving of the drive source based on the manipulation signal received from the control unit 5.

In this embodiment, the master arm 2 and the slave arm 3 each include three arms. However, in practice, the master arm 2 and the slave arm 3 may each have one or more arms. The number of arms included in the master arm 2 and the slave arm 3 may not be identical to each other, and the directions of the rotation axes thereof may differ.

Figure 2:
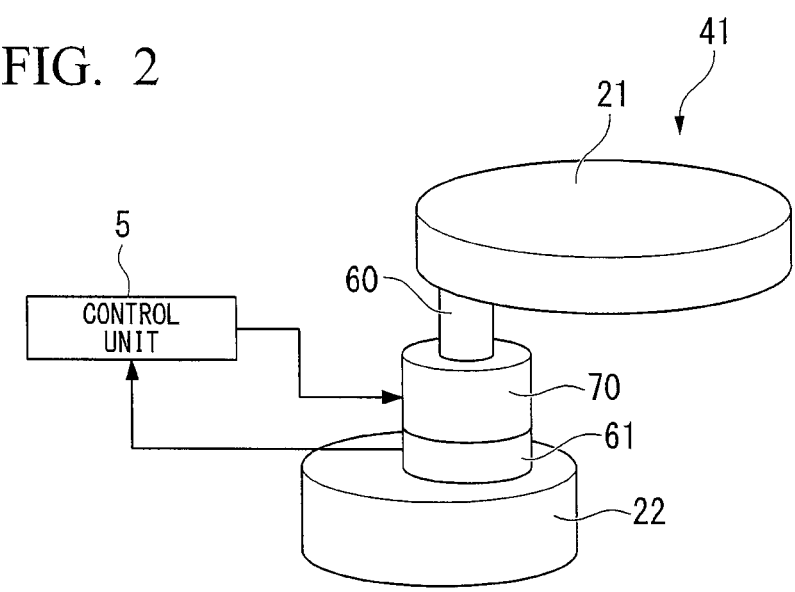
FIG. 2 is a schematic perspective view showing a structure of a first joint part of the master slave manipulator to which the motion mechanism according to the first embodiment of the invention is applied.

FIG. 2 is a schematic perspective view that shows a structure of the first joint part 41 of the maser arm 2. The first joint part 41 includes a shaft part 60 and a drive source 70. The shaft part 60 is fixed to the first arm 21 that is held by the operator Op. The drive source 70 adjusts the manipulation resistance by causing the driving force to act on the shaft part 60.

One end section of the shaft part 60 is fixed to the first master arm 21, and the other end section thereof is rotatably supported by the second master arm 22. The detection part 61 detects a rotational angular speed (an amount of motion) of the shaft part 60. In the vicinity of the shaft part 60, the detection part 61 is fixed to the second master arm 22 and is placed so as not to be rotated with the shaft part 60. As the detection part 61, a known linear encoder or the like may be used.

The drive source 70 is fixed to the second master arm 22 via the detection part 61. A driving part of the drive source 70 is in contact with the shaft part 60 so that the drive source 70 can cause the driving force to act on the shaft part 60. As the drive source 70, for example, a motor capable of rotating normally or reversely or the like can be used, and the motor may also include a gear or the like.

The detection part 61 and the drive source 70 are connected to the control unit 5. The amount of rotation of the shaft part 60 detected by the detection part 61 is sent to the control unit 5, and the driving signal for driving the drive source 70 is sent from the control unit 5 to the drive source 70.

The motion of the master slave manipulator 1 configured as above will be described.

When the operator Op holds the first master arm 21 and performs the operation input to the master arm 2, the shaft part 60 fixed to the first master arm 21, the second joint part 42, and the base joint part 43 are rotated. The rotational angular speed and the direction of the shaft part 60 are detected by the detection part 61 and are transmitted to the control unit 5. The rotational angular speeds and the directions of the respective joint parts 42 and 43 are also transmitted to the control unit 5.

The control unit 5 specifies the rotational angular speed and the rotation direction (the motion direction) of the shaft part 60, based on information from the detection part 61. Furthermore, the control unit 5 calculates the magnitude and the direction of the driving force generated from the drive source 70 based on a predetermined calculation, and generates the driving signal for generating the driving force in the drive source 70.

Figure 3A:
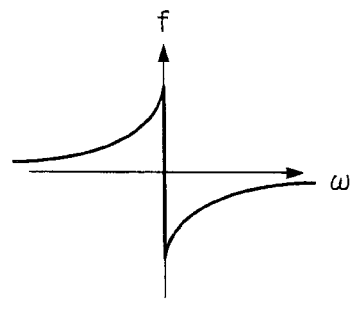
FIG. 3A is a graph showing a relationship between a rotational angular speed of a shaft part of the first joint part and a driving force generated in a drive source, in a control unit of the master slave manipulator to which the motion mechanism according to the first embodiment of the invention is applied.

FIG. 3A is a graph that shows a driving force setting pattern that is a relationship between a rotational angular speed $\omega$ of the shaft part and a magnitude (an absolute value) of the driving force f. A horizontal axis thereof indicates the rotational angular speed $\omega$, wherein a predetermined normal rotation direction, for example, clockwise when the shaft part 60 is viewed from the first master arm 21 side, is positive, and the rotation in the reverse rotation direction opposite the normal rotation direction is negative. A vertical axis thereof indicates the driving force f, wherein a force rotating the shaft part 60 normally is positive, and a force rotating the shaft part 60 in reverse is negative.

As will be understood with reference to FIG. 3A, in the control unit 5, the magnitude and the direction of the driving force f are set so that a great driving force opposite the rotational angular speed is generated in the drive source 70 as the absolute value of the rotational angular speed $\omega$ is reduced. That is, as the absolute value of the rotational angular speed $\omega$ is reduced, the manipulation resistance when performing the operation is increased.

The driving signal generated by the control unit 5 is transmitted to the drive source 70. When the drive source 70 is driven based on the driving signal, the driving force f with the magnitude and the direction set by the control unit 5 is generated, and the manipulation resistance of the master arm 2 is adjusted.

The setting of the driving force f and the generation and the transmission of the driving signal are repeatedly performed at predetermined intervals, for example, dozens of microseconds. The rotational angular speed $\omega$ used in the setting is detected as a difference from the state of the shaft part 60 at the time of the setting of the driving force immediately before.

As described above, according to the master slave manipulator 1 according to the embodiment, the control unit 5 generates the driving force f of a predetermined direction and magnitude in the drive source 70 based on the rotational angular speed $\omega$ of the shaft part 60 of the first joint part 41 using the operation input of the operator Op to the master arm 2, and the control unit 5 gives the master arm 2 the manipulation resistance depending on the rotational angular speed $\omega$.

The driving force f is set in a state as the graph shown in FIG. 3A. For this reason, for example, like the motion of applying the needle, in a case in which the first master arm 21 is gradually moved at the rotational angular speed having a small absolute value, the manipulation resistance is set so as to increase with a relatively great level and the manipulation resistance is stabilized. Meanwhile, like a treatment that stops bleeding, when the first master arm 21 is moved at the rotational angular speed of a large absolute value, the manipulation resistance is set to a relatively small level, which prevents the rapid operation of the operator from being disturbed. That is, depending on the operation input to the master arm 2, the manipulation resistance is suitably adjusted in conjunction with the contents of the operation. For this reason, an appropriate manipulation resistance is constantly generated in the master arm 2. As a result, stress of the operator is reduced, and thus the operator can easily and suitably perform various operations.

Figure 3B:
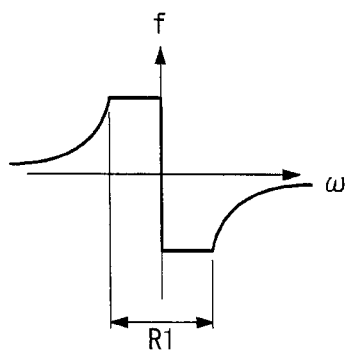
FIG. 3B is a graph showing the relationship between the rotational angular speed of the shaft part of the first joint part and the driving force generated in the drive source, in the control unit of the master slave manipulator to which the motion mechanism according to the first embodiment of the invention is applied.

In this embodiment, the driving force setting pattern is not limited to that shown in FIG. 3A. Thus, as shown on FIG. 3B, when the absolute value of the rotational angular speed $\omega$ is within a predetermined range R1, that is, the amount of motion of the master arm is equal to or less than a predetermined threshold value, the value of the driving force f may be fixed to a predetermined value that is relatively larger than the predetermined range R1.

Figure 4A:
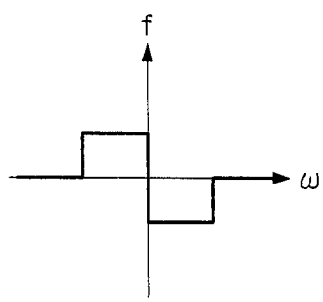
FIG. 4A is another example of the graphs of FIGS. 3A and 3B.
Figure 4B:
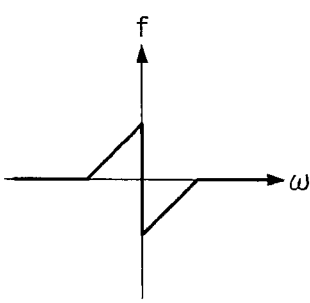
FIG. 4B is another example of the graphs of FIGS. 3A and 3B.
Figure 4C:
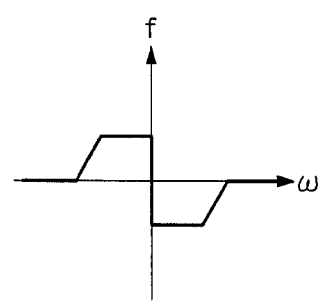
FIG. 4C is another example of the graphs of FIGS. 3A and 3B.

As shown in FIGS. 4A to 4C, when the absolute value of the rotational angular speed $\omega$ is equal to or greater than a predetermined value, the driving force f may be zero, that is, the driving force f may be set so that the drive source 70 is not driven. In the case of the aspect shown in FIG. 4A, a sudden change of a feeling of resistance is felt by an operator. For this reason, as an example, usage in a situation in which the operator desires to consciously discriminate between a case of performing a light and quick operation and a case of performing a careful and minute operation will be considered. In the case of the aspect shown in FIG. 4B, the smaller the absolute value of the amount of motion is, the greater the feeling of resistance is. Therefore, as an example, usage in a situation in which minute operation is included in the case in which more minute operation is required will be considered. In the case of the aspect shown in FIG. 4C, the change of feeling of resistance to the amount of motion is continuous, and it is difficult for the operator to feel the change. For that reason, as an example, usage in a situation in which the operator unconsciously performs rapid operation and careful operation will be considered.

Figure 5A:
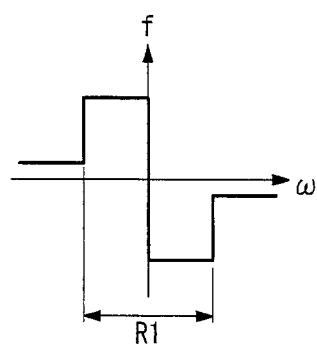
FIG. 5A is another example of the graphs of FIGS. 3A and 3B.

Furthermore, as shown in FIG. 5A, when the absolute value of the rotational angular speed $\omega$ is beyond a predetermined range R1, the value of the driving force f may be set to a value that is smaller than the predetermined range R1 but is not zero.

In addition, although it is not shown, when the absolute value of the rotational angular speed $\omega$ is equal to or greater than a predetermined value, the value of the driving force f may be set in the same direction as the rotational angular speed $\omega$. In this case, when the absolute value of the rotational angular speed $\omega$ is equal to or greater than a predetermined value, since the driving force f serves to assist rotation of the shaft part 60 in the same direction as that of the operation input, the manipulation resistance is lightened and can assist the quick operation of the operator.

Figure 5B:
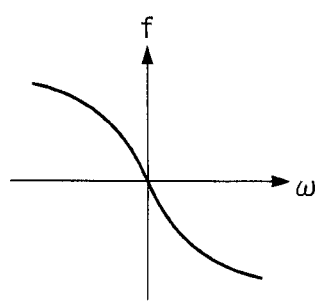
FIG. 5B is another example of the graphs of FIGS. 3A and 3B.

Furthermore, as shown in FIG. 5B, the value of the driving force f may be set so as to be increased as the absolute value of the rotational angular speed ω is increased. In this case, the smaller the amount of motion is, the more the ratio of the change of the driving force f to the change of the amount of motion is increased. For this reason, for example, when the amount of motion is the rotational angular speed, the smaller the manipulating speed is, the heavier the feeling of resistance to the acceleration and the deceleration is, and thus stable motion can be performed.

A second embodiment of the invention will be described with reference to FIG. 6. A master slave manipulator according to the present embodiment is different from the master slave manipulator 1 mentioned above in that further including a switch for switching the setting form of the manipulation resistance. In the description mentioned below, configurations common to those mentioned above will be references by the same reference numerals and description thereof will be omitted.

Figure 6:
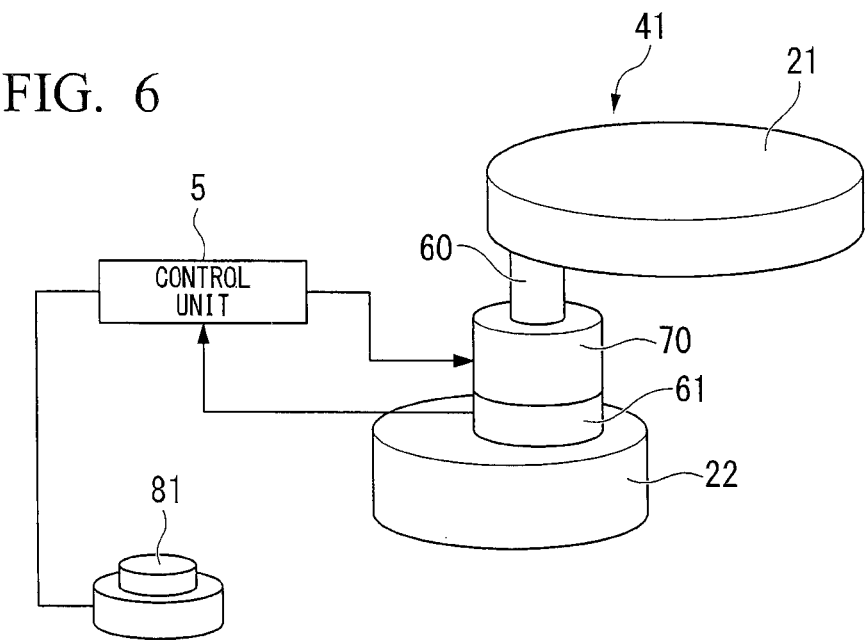
FIG. 6 is a schematic perspective view showing a structure of a first joint part of a master slave manipulator according to a second embodiment of the invention.

FIG. 6 is a schematic perspective view that shows a configuration of the first joint part 41 of the master slave manipulator according to this embodiment. A switch 81 is connected to the control unit 5. The switch 81 constitutes a part of the operation part, and if the switch is in a position where it can be operated by the operator Op, the placement position and the form thereof are not particularly limited. The switch 81 may be, for example, provided in the first master arm 21.

In the present embodiment, unlike the first embodiment, the control unit 5 sets the direction and the magnitude of the driving force f depending on the mode set in the respective points of time. As the mode, two modes including a first mode and a second mode are provided. In the first mode, a driving force $f_1$ of a predetermined magnitude in a direction opposite to the rotational angular speed ω is set. In the second mode, a driving force $f_2$ smaller than the driving force $f_1$ in the direction opposite to the rotational angular speed ω is set.

The mode set in the control unit 5 is switched by the operation of the switch 81. That is, the operator Op operates the switch 81 with his or her hand, and thus the currently set mode is switched to the other mode.

In the master slave manipulator according to the present embodiment, the control unit 5 sets the direction and the magnitude of the driving force f based on the rotation direction of the shaft part 60 received from the detection part 61 and the mode set in the control unit 5 at that point in time, generates the driving signal based on the direction and the magnitude, and transmits the driving signal to the drive source 70.

Even in the master slave manipulator according to the present embodiment, an operator Op operates the switch 81 and appropriately sets the mode of the control unit 5. Thus, as in the first embodiment, it is possible to constantly give an appropriate manipulation resistance to the master arm 2. Thus, the operator can easily and suitably perform various operations.

Furthermore, in the master slave manipulator according to the present embodiment, the operation part includes the switch 81. For this reason, the operator Op can actively switch the mode to a mode suitable for the operation currently being performed or to a mode suitable for an operation to be performed next. Thus, it is possible to apply suitable manipulation resistance to the master arm 2 more reliably.

In the present embodiment, the number of modes is not limited to two. Accordingly, in order to enable adjustment of the more careful manipulation resistance, three or more modes may be provided.

Furthermore, the contents of the modes are not limited to those that constantly generate the driving force of the fixed size as mentioned above. For example, as in the first embodiment, the driving force setting pattern, in which the magnitude of the driving force is changed according to the direction and the magnitude (the absolute value) of the rotational angular speed ω, may be used as the mode. Such mode may be provided in the control unit 5 so as to be combined with the mode that constantly generates the driving force of the fixed magnitude.

Furthermore, the type of switch is not limited to a button type as shown in FIG. 6, but various types of switches can be used. For example, a foot switch, a trigger type switch, a switch of a graphical user interface (GUI) displayed on a display part or the like can be adopted. Furthermore, it is possible to adopt a switch not requiring a physical switch mechanism such as a sound switch that identifies the voice of the operator and switches the mode, and a "body switch" that detects a position and an orientation of specific body parts such as a head or a finger of the operator and switches the mode.

A third embodiment of the invention will be described with reference to FIGS. 7 to 9C. The master slave manipulator according to the present embodiment is different from the master slave manipulators according to the respective embodiments mentioned above in some points including the setting form of the driving force.

Figure 7:
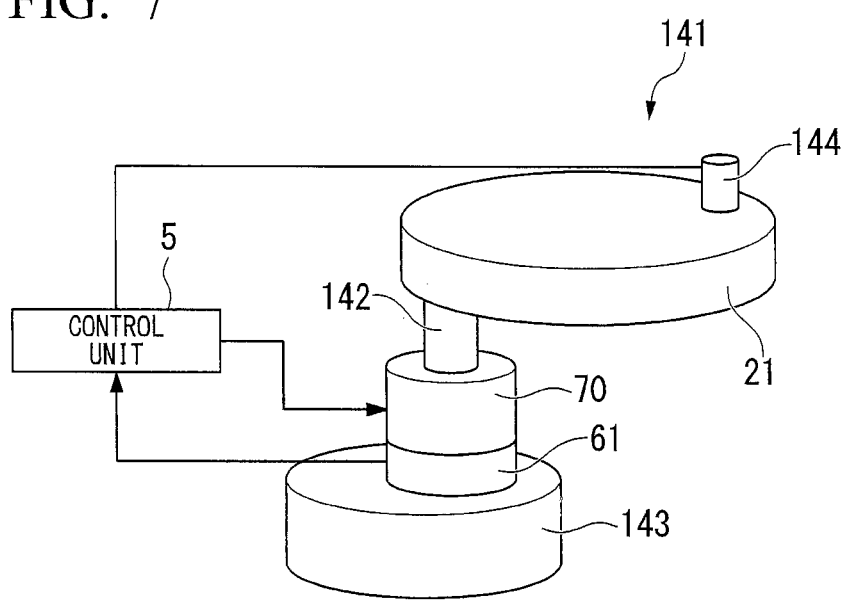
FIG. 7 is a schematic perspective view showing a structure of a first joint part of a master slave manipulator according to a third embodiment of the invention.

FIG. 7 is a schematic perspective view that shows a structure of a first joint part 141 of the master slave manipulator according to the present embodiment. Configurations of a shaft part 142 and a second master arm 143 are substantially the same as those of the shaft part 60 and the second master arm 22. However, in the master slave manipulator according to the present embodiment shown in FIG. 7, when the drive source 70 is not operated, the manipulation resistance of the first master arm 21 is greater than that in the first joint part 141. For this reason, when the drive source 70 is not operated, it is possible to stably perform the operation such that the first master arm 21 moves bit by bit at the rotational angular speed of the small absolute value, without causing jiggle hand or the like.

In the control unit 5, same as the second embodiment, two modes are provided. However, as mentioned above, since the manipulation resistance of the first joint part 141 is great, in the first mode and the second mode according to the present embodiment, the direction of the generated driving force f is set in the same direction as the rotational angular speed ω. That is, the driving force f acts on the shaft part 142 so as to reduce the manipulation resistance, and the greater the driving force f is, the smaller the manipulation resistance is.

Figure 8A:
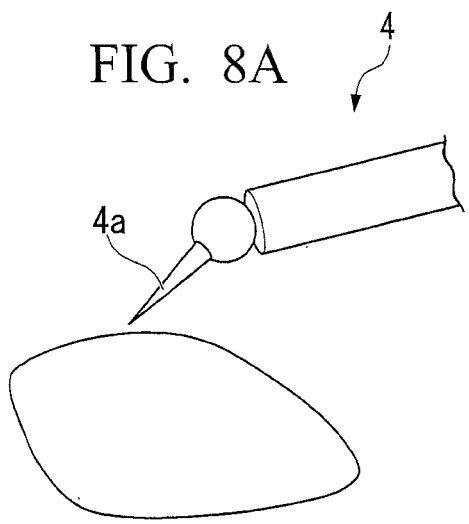
FIG. 8A is a diagram showing a distal end part of a surgical tool.
Figure 8B:
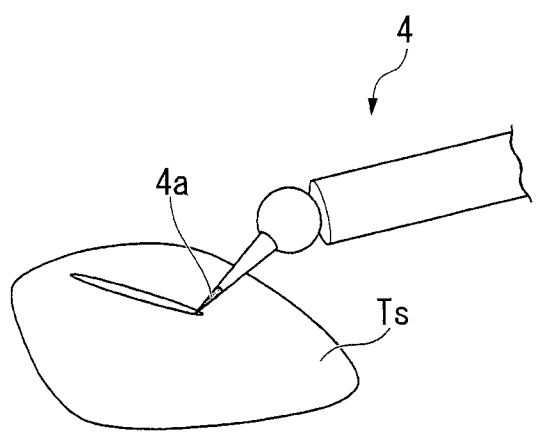
FIG. 8B is a diagram showing the distal end part of the surgical tool.

The surgical tool 4 according to the present embodiment is a high-frequency incision instrument (an energy device) shown in FIG. 8A. When the operator Op presses an electric conduction switch 144 provided in the first master arm 21, a high-frequency current is supplied to the distal end 4A of the surgical tool 4, and enters an active state, and as shown in FIG. 8B, the tissue Ts can be cauterized and cut.

The electric conduction switch 144 is connected to the control unit 5, and an information of an on-off state of the electric conduction switch 144 is sent to the control unit 5.

In the master slave manipulator according to the present embodiment, the mode of the control unit 5 is switched depending on the on-off state of the electric conduction switch 144. When the electric conduction switch 144 is turned on, the second mode in which a smaller driving force is generated is set in the control unit 5, stability of the operation manipulation performed in the active state of the surgical tool 4, such as the tissue is cauterized and cut, is secured. Meanwhile, when the electric conduction switch 144 is turned off, the mode of the control unit 5 is set to the first mode, the manipulation resistance is reduced, and it is easy to rapidly move the surgical tool 4.

In the master slave manipulator according to the present embodiment, the switching of the electric conduction switch 144 for changing the surgical tool 4 to the active state is linked with the exchange of the mode of the control unit 5. For this reason, the operator Op can perform the operation under a suitable manipulation resistance by merely manipulating the electric conduction switch 144 along with the operation. That is, there is no need to separately perform the operation for suitably adjusting the manipulation resistance, and it is possible to perform the operation in the state in which the manipulation resistance is adjusted to a suitable state by the same operation as that of the related art.

Figure 9A:
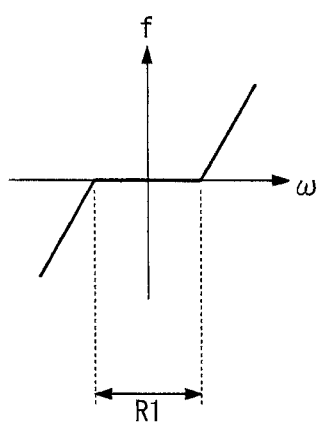
FIG. 9A is a graph showing the relationship between a rotational angular speed of a shaft part of the first joint part and a driving force generated in a drive source, in a control unit of the master slave manipulator to which a motion mechanism according to the third embodiment of the invention is applied.
Figure 9B:
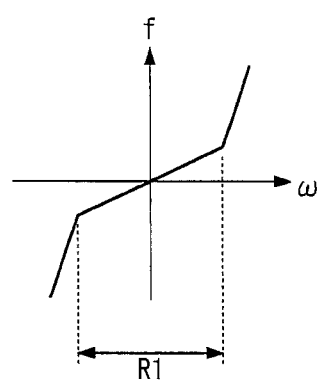
FIG. 9B is a graph showing the relationship between the rotational angular speed of the shaft part of the first joint part and the driving force generated in the drive source, in the control unit of the master slave manipulator to which the motion mechanism according to the third embodiment of the invention is applied.
Figure 9C:
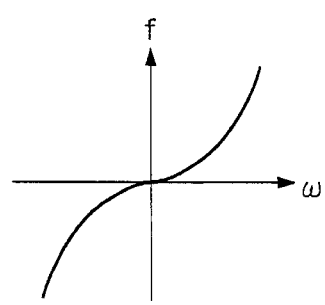
FIG. 9C is a graph showing the relationship between the rotational angular speed of the shaft part of the first joint part and the driving force generated in the drive source, in the control unit of the master slave manipulator to which the motion mechanism according to the third embodiment of the invention is applied.

In addition, like the first joint part 141 according to the present embodiment, when the master arm having the joint structure of the high initial manipulation resistance is controlled only by the driving force setting pattern as in the first embodiment, as shown in FIGS. 9A and 9C, the driving force setting pattern may be configured so that the greater the absolute value of the rotational angular speed ω is, the greater the driving force f in the same direction as the rotational angular speed ω is set. In addition, as shown in FIGS. 9A and 9B, when the absolute value of the rotational angular speed ω is beyond a predetermined range R1, that is, the amount of motion of the master arm is equal to or greater than a predetermined threshold value, the driving force setting pattern in which the greater driving force is set may be used.

The aspect shown in FIG. 9A is used, for example, in a situation in which the initial motion resistance when the amount of motion is small is appropriate in view of the minute operation or the like. The aspect shown in FIG. 9B is used in a case in which there is a need for a reduction in motion resistance to some extent even when the amount of motion is small, because the initial motion resistance is great. In the aspect shown in FIG. 9B or 9C, the minute operation can be performed basically using an initial manipulation resistance. Meanwhile, when the amount of motion is great, by actively generating the driving force to lighten the manipulation resistance, the operation can be lightly performed. Furthermore, in the aspect shown in FIG. 9C, since the slope of an increase in driving force is continuously changed, the operator hardly feels a sense of discomfort and can smoothly perform the operation.

As mentioned above, although the respective embodiments of the invention have been described, the technical scope of the invention is not limited to the embodiments mentioned above, and it is possible to add various modifications to each component, delete them, or combine the configurations of the respective embodiments without departing from the scope of the invention.

For example, in the respective embodiments mentioned above, an example in which the drive source, the detection part or the like are provided only in the first joint part of the master arm has been described. However, such a mechanism may be provided in two or more joint parts, and may be provided in all of the joint parts. When the plurality of joints is included, a case in which the operator operates the distal end of the arm with his or her hand and arm is assumed. However, by setting the driving force suitable for each joint based on the arm length between each of the joints and the initial manipulation resistance, unevenness is not generated depending on the direction, and a feeling of operation using the hand and the arm is improved. Furthermore, for example, when there is an object which is desired not to make contact in a certain direction, in order to reduce the motion of only a specific joint, the driving force can be set so as to enhance the manipulation resistance of the joint.

Furthermore, in the respective embodiments mentioned above, the master slave manipulator in which the operation part is the master arm has been described. However, the operation support device of the invention is not limited thereto, and the operation part may be constituted by a joystick or the like. In this case, the manipulation resistance of the joystick or the like is controlled. Furthermore, the operation part may be wirelessly connected to the control unit.

Furthermore, in a case that the operation support device is constituted such that a plurality of surgical tools, which is attachable and detachable to the action part, is exchangeable, identification information is preserved on each surgical tool and the surgical tool mounted on the action part is identified by the control unit based on the identification information. And then, the corresponding surgical tool is selected from the driving force setting patterns prepared for each kind of surgical tool in advance or the combination of the modes, and the driving signal may be generated based thereon. In this manner, the operation in which the operator performs adjustment of the manipulation resistance is reduced, and thus the operation can be simply and easily performed.

Figure 10:
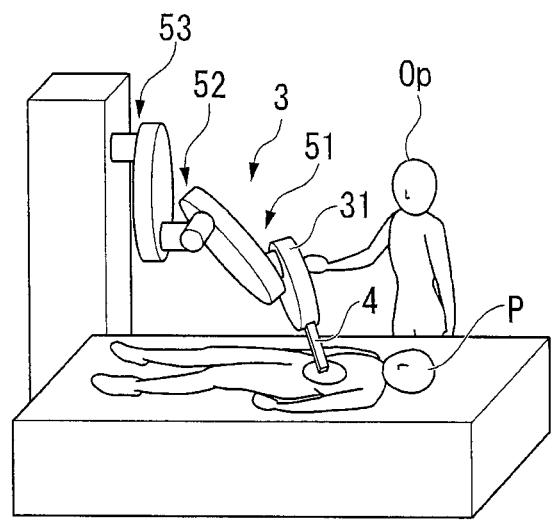
FIG. 10 is a diagram showing an operation support device of a modified example of the embodiments of the invention.

Furthermore, as in a modified example shown in FIG. 10, a part of the slave arm 3 constitutes the operation part and the remainder thereof constitutes the action part, and thus the operation support device may be configured by the slave arm 3 and the surgical tool 4. FIG. 10 shows a case of the first slave arm 31. In this case, means for detecting a force acting on the slave arm and the amount of minute motion when the operator tries to move the slave arm is provided in the slave arm, the amount of detection thereof is subjected to the motion command, and the respective joints 51, 52, and 53 of the slave arm can be configured so as to be operated by the driving force of the drive source. By appropriately setting the driving force, it is possible to adjust the initial manipulation resistance. The detection means may be provided near a location where it is held by a hand or may be provided in the motion mechanism of each joint.

Figure 11:
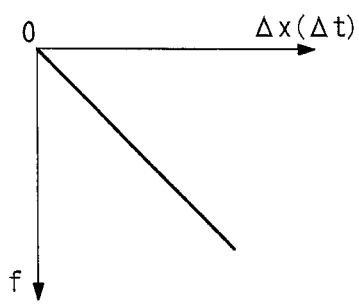
FIG. 11 is a graph showing a relationship between an amount of switch manipulation and a driving force in an operation support device according to another modified example of the embodiments of the invention.

Instead of the amount of motion of the operation part, it is also possible to use the driving force setting pattern which relates the operation aspect of the switch to the setting of the driving force. FIG. 11 is a graph that shows a relationship between a pressing amount Δx of the switch and the driving force f in a modified example of the embodiments mentioned above. In this modified example, the control unit sets the driving force f so that when the pressing amount Δx is increased, the absolute value of the driving force f is increased. In this case, the operator can adjust the manipulation resistance more carefully. In addition, in the modified example, the pressing amount Δx can be detected by providing a sensor or the like in the switch. Furthermore, instead of the pressing amount, it is also possible to associate a time Δt during the switch being pressed with the driving force f.

In the same method, it is also possible to associate an operation aspect of the switch with the switching of the mode.

In addition, the driving force setting pattern and the mode in the invention may be prepared from various viewpoints. For example, the driving force setting pattern and the mode may be prepared for every operator, every operation, and every task pattern. In this case, the operator may input the manipulator ID, the operation, and the task pattern to the operation support device via an interface such as a GUI, and the control unit may be configured so as to select the driving force pattern and the mode depending on the input contents.

While preferred embodiments of the present invention have been described and illustrated above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

What is claimed is:

1. An operation support device which includes an operation part into which an operation is input by a manipulator, and an action part to which a surgical tool is attached and which is driven by the operation input, the operation support device comprising:
    a drive source which is provided in the operation part and generates a driving force which applies the driving force to the operation part;
    a detection part which is provided in the operation part and detects an amount of motion of the operation part in accordance with the operation input; and
    a control unit which sets a magnitude and a direction of the driving force based on the operation input to the operation part when the operation is input, the control unit setting the driving force to generate a manipulation resistance to the operation part, the manipulation resistance being adjusted based on a relationship between an amount of change of the amount of motion and an amount of change of the driving force, the control unit being configured to send an operation signal to the action part, the operation signal corresponding to the driving force which is adjusted depending on the operation resistance.

2. The operation support device according to claim 1, wherein
    the operation part comprises a switch,
    the control unit sets the driving force based on one of a plurality of modes, and
    when the switch is operated by an operator, the mode used when the control unit sets the driving force is switched.

3. The operation support device according to claim 2, wherein the switch is configured to be operated by a hand or a foot of the operator.

4. The operation support device according to claim 2, wherein the surgical tool is in an active state when performing an operation, and
    the switch combines function to switch the surgical tool to the active state.

5. The operation support device according to claim 1, wherein the control unit sets the driving force so that the driving force is increased as the amount of motion is reduced.

6. The operation support device according to claim 5, wherein the control unit sets the driving force so as to relatively increase when the amount of motion is equal to or less than a predetermined threshold value.

7. The operation support device according to claim 1, wherein the control unit sets the driving force so that the driving force is increased as the amount of motion is increased, and the relationship between the amount of change of the amount of motion and the amount of change of the driving force is changed depending on a value of the amount of motion.

8. The operation support device according to claim 7, wherein the control unit sets the driving force so as to be relatively increase when the amount of motion is equal to or greater than a predetermined threshold value.

9. The operation support device according to claim 1, wherein
    the surgical tool is provided in a plural number in the action part in an attachable and detachable manner, and the respective surgical tools have identification information, and
    the control unit sets the magnitude and the direction of the driving force based on the identification information of the surgical tool mounted on the action part.

10. The operation support device according to claim 1, wherein the amount of motion is a rotational angular speed of an arm of the operation part when rotating the arm around an axis by the operation input, and
    the control unit is configured to adjust the operation resistance of the operation part based on a relationship between the rotational angular speed and the driving force.

* * * * *